(12) United States Patent
Qader

(10) Patent No.: US 6,638,574 B1
(45) Date of Patent: Oct. 28, 2003

(54) WOOD PRESERVATION

(75) Inventor: Abdul Qader, Doncaster (AU)

(73) Assignee: Commonwealth Scientific and Industrial Research Organisation (AU)

( * ) Notice: Subject to any disclaimer, the term of this patent is extended or adjusted under 35 U.S.C. 154(b) by 0 days.

(21) Appl. No.: 10/031,203

(22) PCT Filed: Jun. 29, 2000

(86) PCT No.: PCT/AU00/00740

§ 371 (c)(1),
(2), (4) Date: Jan. 10, 2002

(87) PCT Pub. No.: WO01/05564

PCT Pub. Date: Jan. 25, 2001

(30) Foreign Application Priority Data

Jul. 14, 1999 (AU) .............................................. PQ1607

(51) Int. Cl.[7] .................................................. B05D 7/06
(52) U.S. Cl. .......................................................... 427/384
(58) Field of Search ............................................ 427/384

(56) References Cited

U.S. PATENT DOCUMENTS 4,992,308 A * 2/1991 Sunol ........................ 427/297
5,094,892 A * 3/1992 Kayihan .................... 427/440

FOREIGN PATENT DOCUMENTS

| DE | 4404839 | * | 8/1995 |
| FR | 2 754 464 | | 4/1998 |
| FR | 2770171 | * | 4/1999 |
| JP | 59-101311 | * | 6/1984 |

OTHER PUBLICATIONS

Acda et al, Material und Organismen, 30(4), pp. 293–300, 1996.*

Smith et al, Wood Fiber Sci., 25(2), pp. 119–123, 1993.*

* cited by examiner

*Primary Examiner*—Erma Cameron
(74) *Attorney, Agent, or Firm*—Dinsmore & Shohl LLP

(57) ABSTRACT

A method of and a composition for treating wood with an insecticide. The composition comprises an insecticide such as a pyrethroid dissolved in a supercritical fluid such as carbon dioxide. The composition may also include a co-solvent such as methanol. The method includes impregnating wood with the composition and reducing the temperature and pressure below critical levels to precipitate the insecticide within the wood.

20 Claims, 2 Drawing Sheets

WOOD PRESERVATION

CROSS-REFERENCE TO RELATED APPLICATIONS

Priority filing benefit of (1) International PCT application PCT/AU00/00740, filed Jun. 29, 2000, and published in the English language, on Jan. 25, 2001 with International Publication No. WO 01/05564 A1; and (2) Australian Application No. PQ1607, filed Jul. 14, 1999.

The present invention relates to a method and composition for the treatment of wood and wood products and more particularly the treatment of wood with an insecticide.

In particular environments terrestrial borers such as termites have been known to readily damage timber products. Therefore, timber products are often impregnated with insecticides, preferably pyrethroids so as to control borer, termite, and other insecticidal damage.

An insecticide such as a pyrethroid may be impregnated into timber in the presence of hydrocarbon solvents, aqueous solutions, emulsions and microemulsions, and dispersions. However, many refractory timbers are resistant to impregnation due to the high surface tensions of the solvents that inhibit flow into the microporous structure of timber, even if external pressure is applied. Therefore, the existing methods of impregnating insecticides such as pyrethroids into timber in the presence of any of the previously mentioned carriers does not give satisfactory penetration of preservatives into the heartwood of many softwoods and hardwoods, and for some species the sapwood as well.

Similarly, many wood composites cannot be treated in final form due to barriers to liquid flow resulting from the presence of glue and refractory heartwood or sapwood. The result is often a thin envelope treatment of an insecticide such as a pyrethroid that termites in particular can readily penetrate, allowing them access to an untreated core.

Supercritical fluids have been used for the deposition of various materials onto or into a substrate, however, there have been relatively few publications disclosing the use of supercritical fluids in the treatment of wood and wood products.

Ito et al. in Japanese Pat No. 59-101311 provides the first suggestion of using supercritical fluid to treat wood, however, the disclosure provides few details and no examples to show how the method would work in practice. Subsequent studies suggest that many of the stated objectives were not achieved (Morrell et al., American Wood-Preservers' Association 1997, 93, April, pp. 367–386).

Sunol in U.S. Pat. No. 4,992,308 discloses a method and process using a supercritical fluid, with or without the aid of entrainers to solubilize a monomer, monomer mixture or polymer, to carry the supercritical solvent mixture thereby created into the wood matrix, to remove extractives from the wood, to precipitate the monomer or polymer within the wood, and to polymerise the monomer in situ in the wood. Polymerisable monomers included methyl methacrylate (MMA), dialkylphthalate, ethyl acrylate, styrene, and many others. Other patents are also referred to in the Sunol patent. These showed examples of treatments for wood and other porous materials, but all of the disclosures dealt with monomers and polymers. These examples did not include insecticides, as the applications of the inventions disclosed in the various patents related specifically to the improvement of mechanical properties of wood such as hardness and bending strength rather than durability against biological agents.

Kayihan in U.S. Pat. No. 5,094,892 discloses a method that can be used in the impregnation of lumber or structural timbers with a preservative, however, the specification did not disclose an example of impregnation with a preservative, rather only with a dye. Also, the Kayihan patent only applies to a chemical that is insufficiently soluble in supercritical carbon dioxide.

Morrell et al., Canadian Wood Preservers Association, 1993, No. 14, pages 6 to 25 discussed the potential of using supercritical fluid processes to treat wood, but all discussion and examples related to fungicides.

It would appear that no prior study has examined the feasibility of impregnating wood or wood products with insecticides including the pyrethroids. Nor have they determined whether a co-solvent is required, or provided examples of successful wood treatment processes.

It is therefore an object of the invention to provide a method and composition for the treatment of wood with an insecticide using a supercritical fluid.

According to a first aspect of the invention there is provided a method of treating wood with an insecticide, including impregnating intact wood with an effective amount of an insecticide in the presence of a supercritical fluid under conditions that enable sufficient insecticide to dissolve in the supercritical fluid.

In a preferred embodiment of the first aspect of the invention, the method includes treating wood with an insecticide, the method including the steps of:

passing a supercritical fluid through a bed of insecticide to form a solution of insecticide in the supercritical fluid, impregnating wood with the solution at a temperature and pressure in excess of supercritical levels and decreasing the temperature and pressure below supercritical levels to precipitate the insecticide within the impregnated wood.

It is preferred that the pyrethroid is any one of permethrin, cypermethrin or deltamethrin, though other pyrethoids may be utilised in the wood treatment process. The insecticides may also be impregnated in conjunction with fungicides.

Supercritical fluid ceases to be a liquid and behaves like a gas, although retaining the solvent properties of a liquid. Though it is preferred that the supercritical fluid utilised in the wood treatment process is carbon dioxide, other supercritical fluids can be utilised.

Carbon dioxide at a temperature greater than its critical temperature of 31.1° C. and a critical pressure of 72.9 atm. or 7.39 MPa is widely used as a supercritical fluid. This is due essentially to the fact that supercritical carbon dioxide has a relatively low critical pressure and temperature, low cost, is readily available in large quantities, and is non-toxic, odourless, and non-flammable. Its surface tension becomes zero with a viscosity of about 320 $\mu$P (at 40° C. and 75.1 atm.). It has very good solvent characteristics and is environmentally sound without having any pollution and waste disposal problems.

In determining the suitability of supercritical fluid technology as a carrier for various chemicals, solubility is probably the most important thermophysical property that must be acquired and modelled for an efficient design of any industrial scale impregnator (Ashraf-Khorassani et al., 1997; Madras et al., 1993). Both temperature and pressure can affect the solubility of a solute in a supercritical fluid (Schmitt and Reid, 1986). Raising the temperature can dramatically increase the vapour pressure of the solute and consequently its solubility (Miller and Hawthorne, 1994). Hence, the solubility must be determined as a function not only of pressure, but also of temperature (Hampson, 1996).

A co-solvent may be used to increase the solubility of a particular insecticide in supercritical fluid. Suitable co-solvents include alcohols, but methanol is preferred.

According to a second aspect of the invention, there is provided a composition for treating wood, the composition including an effective amount of an insecticide dissolved in a supercritical fluid.

Preferably the supercritical fluid is carbon dioxide and the insecticide is a pyrethroid. It is preferred that the pyrethroid is any one of permethrin, cypermethrin or deltamethrin, though other pyrethoids may be utilised.

Preferably the composition includes a co-solvent. The co-solvent may be an alcohol and is preferably methanol.

BRIEF DESCRIPTION OF THE DRAWINGS

The present invention is further explained with respect to the following figures and examples.

EXAMPLE 1

Solubility Studies

In this work, the solubilities of a group of insecticides (the synthetic pyrethroids permethrin, deltamethrin and cypermethrin) in supercritical carbon dioxide with and without a co-solvent have been determined using an on-line SFE system incorporating a recirculation pump to achieve efficient mixing under static conditions. The on-line analysis of solubilised insecticide (using HPLC) was performed to obtain accurate and reliable solubility data. The solubilities of anthracene were first tested to ensure system reliability and were found to agree well with published results. The range of pressure used was 80–280 bars at three different temperatures of 40, 50 and 60° C. The acquired solubility data for the insecticides, with or without co-solvent, were found to be more than sufficient for impregnating timber.

Figure 1:
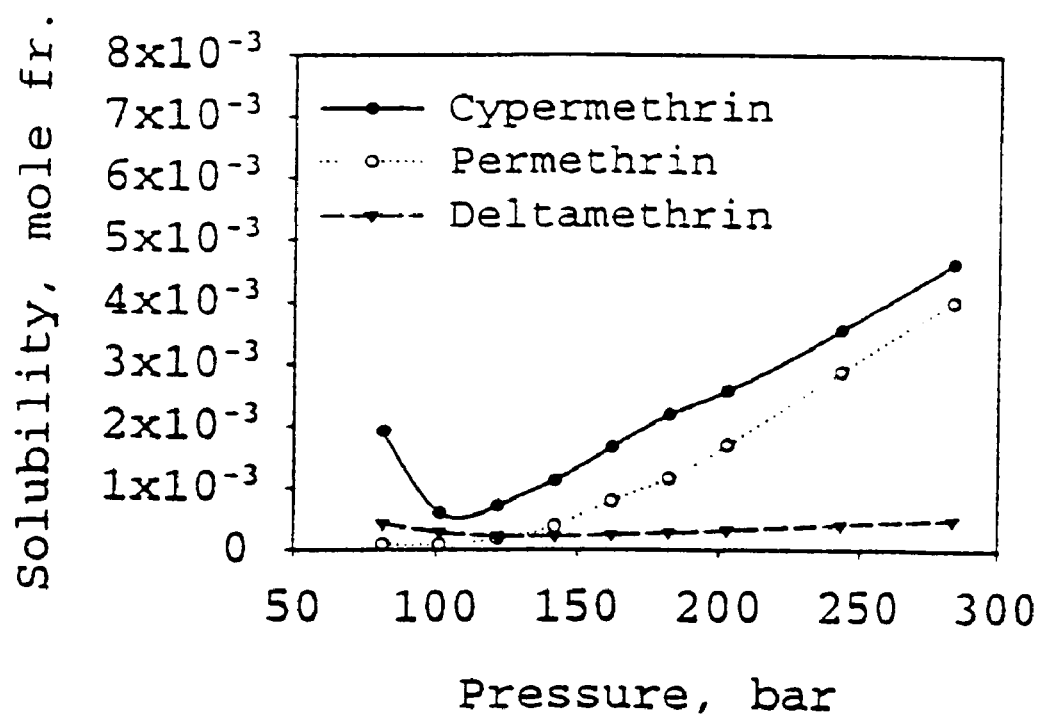
FIG. 1 is a graph showing the solubility of 3 pyrethroids at a range of pressures, a temperature of 50° C. and in the absence of a co-solvent.
Figure 2:
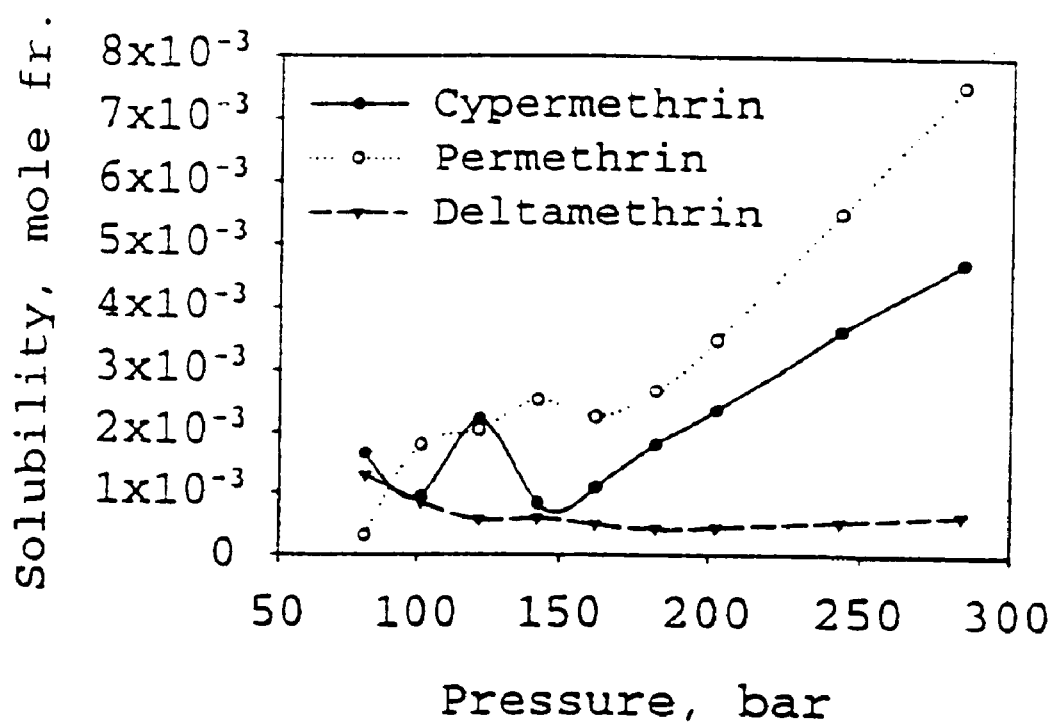
FIG. 2 is a graph of solubility versus pressure at 50° C. in the presence of a co-solvent for several pyrethroids.

As a trend, solubility increased dramatically with pressure and was enhanced by higher temperature. Among all the temperatures studied here, 50° C. showed the highest solubility values and may be considered the favourable condition for solubilising pyrethroids in supercritical carbon dioxide for timber treatment. A comparison of solubility values between the three pyrethroids showed that solubilities for deltamethrin were lowest in almost all cases and those for cypermethrin and permethrin were higher by 1 to 8 times irrespective of the use of co-solvent. The additional functional group —CN in deltamethrin and more importantly, its specific rotational characteristic, are considered to be responsible for its differing behaviour. Cypermethrin's solubility without co-solvent was more than 20% higher than the corresponding value for permethrin at all pressures. However, when 5% methanol was used the results for cypermethrin and permethrin were opposite. These facts are illustrated in FIGS. 1 and 2. Again the presence of the —CN group in cypermethrin is believed to be the main reason for the differing solubility.

In general, addition of methanol as a co-solvent increased solubility. Polarity of methanol had considerable advantage.

EXAMPLE 2

Impregnation Tests

In principle, a SF (supercritical fluid) such as carbon dioxide (mixed with or without a co-solvent) is circulated through a bed of insecticide until the solution is saturated. This fluid is introduced into the vessel containing wood. After achieving required supercritical conditions and the insecticide has completely penetrated the wood, the temperature or pressure is decreased below the critical value. The insecticide loses solubility and precipitates inside the wood. The carbon dioxide is then released via separator/s where the remaining insecticide is precipitated out. The treatment is thus complete. Supercritical treatment has been applied to a variety of timber blocks that were of dimension 200×35×35 mm, e.g., messmate (*Eucalyptus obliqua*) heartwood, pine (*Pinus radiata*) sapwood, LVL (laminated veneer lumber) of pine (*P. radiata*), LVL of Douglas fir (*Pseudotsuga menziesii*) and MDF (medium density fibreboard).

Conclusion

The experiments have shown that the insecticides can be injected deep into the core of timber samples (Table 1), at levels well above the required level for hazard classes 1 to 3 (Table 2) currently used in timber treatment.

TABLE 1

Permethrin retention in the core of the timber samples

| Sample | Permethrin retention as % mass/mass based upon the oven-dried mass of the treated wood |
|---|---|
| *Pinus radiata* sapwood | 0.09 to 0.21 |
| *Eucalyptus obliqua* heartwood | 0.03 to 0.10 |
| *P. radiata* LVL | 0.04 to 0.15 |
| *P. menzeisii* LVL | 0.08 to 0.15 |
| MDF | 0.03 to 0.05 |

TABLE 2

Minimum preservative retention required in the penetration zone [Extracted from AS 1604 -1997]

| | Minimum preservative retention as % mass/mass based upon the oven-dried mass of the treated wood | | |
|---|---|---|---|
| Synthetic pyrethroid | Hazard class 1 (H1) | Hazard class 2 (H2) | Hazard class 3 (H3) |
| Permethrin | 0.0060 | 0.020 | 0.020 |
| Cypermethrin | 0.0060 | 0.030 | 0.030 |
| Deltamethrin | 0.0006 | 0.002 | 0.002 |

Those skilled in the art will appreciate that the inventions described herein may be susceptible to variations and modifications other than those specifically described. It will be appreciated that the invention is to be understood to include all such variations and modifications that fall within the spirit and scope.

What is claimed is:

1. A method of treating wood with an insecticide, comprising
   dissolving an insecticide in a supercritical fluid to form a solution of the insecticide in the supercritical fluid; and
   impregnating intact wood or wood products with an effective amount of the solution, wherein the insecticide is a pyrethroid.

2. A method according to claim 1, wherein the supercritical fluid is supercritical carbon dioxide.

3. A method according to claim 2, wherein the insecticide is dissolved in the supercritical carbon dioxide at a temperature in a range from 40° C. to 60° C. and a pressure in excess of 150 bar.

4. A method according to claim 2, wherein the insecticide is permethrin, wherein the solution further comprises methanol as a co-solvent, and wherein the permethrin is dissolved in the supercritical carbon dioxide at a temperature in a range from 40° C. to 60° C. and a pressure in excess of 100 bar.

5. A method according to claim 2, wherein the insecticide is deltamethrin, wherein the solution further comprises methanol as a co-solvent, and wherein the deltamethrin is dissolved in the supercritical carbon dioxide at a temperature in a range from 40° C. to 60° C. and a pressure in a range from 80 to 280 bar.

6. A method according to claim 2, wherein the insecticide is cypermethrin, wherein the solution further comprises methanol as a co-solvent, and wherein the cypermethrin is dissolved in the supercritical carbon dioxide at a temperature in a range from 40° C. to 60° C. and a pressure in a range from 100 to 280 bar.

7. A method according to claim 3, wherein the temperature is about 50° C.

8. A method according to claim 1, wherein the pyrethroid is selected from a group consisting of permethrin, cypermethrin and deltamethrin.

9. A method according to claim 1, wherein the insecticide is accompanied with a fungicide.

10. A method according to claim 1, wherein the solution further comprises a co-solvent.

11. A method according to claim 10, wherein the co-solvent is an alcohol.

12. A method according to claim 11, wherein the alcohol is methanol.

13. A method according to claim 1, further comprising:
    passing the supercritical fluid through a bed of insecticide to dissolve the insecticide in the supercritical fluid, and after impregnating the intact wood or wood products with the solution, decreasing the temperature and pressure below supercritical levels to precipitate the insecticide within the impregnated wood or wood products.

14. A method of treating wood with an insecticide, comprising
    dissolving an insecticide in a supercritical fluid and a co-solvent to form a solution of the insecticide in the supercritical fluid, wherein the insecticide is a pyrethroid; and
    impregnating intact wood or wood products with an effective amount of the solution.

15. A method according to claim 14, wherein the co-solvent is an alcohol.

16. A method according to claim 15, wherein the alcohol is methanol.

17. A method according to claim 14, wherein the supercritical fluid is supercritical carbon dioxide.

18. A method according to claim 17, wherein the insecticide is dissolved in the supercritical carbon dioxide at a temperature in a range from 40° C. to 60° C. and a pressure in excess of 150 bar.

19. A method according to claim 14, wherein the pyrethroid is selected from a group consisting of permethrin, cypermethrin and deltamethrin.

20. A method according to claim 14 comprising:
    passing the supercritical fluid through a bed of insecticide to dissolve the insecticide in the supercritical fluid and the co-solvent; and
    after impregnating the intact wood or wood products with the solution, decreasing the temperature and pressure below supercritical levels to precipitate the insecticide within the impregnated wood or wood products.

* * * * *